(12) United States Patent
Yokobori et al.

(10) Patent No.: US 9,177,400 B2
(45) Date of Patent: Nov. 3, 2015

(54) PROGRAM, MEDIUM, AND DEVICE FOR DETERMINING VASCULAR DISEASE

(75) Inventors: Toshimitsu Yokobori, Miyagi (JP); Daisuke Tanaka, Miyagi (JP); Yuuki Tomono, Miyagi (JP); Masatoshi Ito, Miyagi (JP); Yuji Otomo, Miyagi (JP)

(73) Assignee: TOHOKU TECHNOARCH CO., LTD., Miyagi (JP)

( * ) Notice: Subject to any disclaimer, the term of this patent is extended or adjusted under 35 U.S.C. 154(b) by 364 days.

(21) Appl. No.: 13/809,673

(22) PCT Filed: Feb. 28, 2011

(86) PCT No.: PCT/JP2011/054451
§ 371 (c)(1),
(2), (4) Date: Mar. 5, 2013

(87) PCT Pub. No.: WO2012/008173
PCT Pub. Date: Jan. 19, 2012

(65) Prior Publication Data
US 2013/0169646 A1  Jul. 4, 2013

(30) Foreign Application Priority Data
Jul. 14, 2010  (JP) .................................. 2010-159797

(51) Int. Cl.
*G06T 11/20* (2006.01)
*A61B 8/08* (2006.01)

(52) U.S. Cl.
CPC ............. *G06T 11/206* (2013.01); *A61B 8/0891* (2013.01); *A61B 8/488* (2013.01); *A61B 8/5207* (2013.01)

(58) Field of Classification Search
None
See application file for complete search history.

(56) References Cited

U.S. PATENT DOCUMENTS

| | | | |
|---|---|---|---|
| 2003/0121330 A1* | 7/2003 | Muhle et al. ..................... | 73/600 |
| 2007/0055151 A1* | 3/2007 | Shertukde et al. ............ | 600/437 |
| 2010/0121624 A1* | 5/2010 | Roy et al. .......................... | 703/6 |
| 2010/0121801 A1* | 5/2010 | Roy et al. ........................ | 706/46 |
| 2011/0314544 A1* | 12/2011 | Shin et al. ....................... | 726/23 |

* cited by examiner

*Primary Examiner* — Phi Hoang
(74) *Attorney, Agent, or Firm* — Birch, Stewart, Kolasch & Birch, LLP

(57) ABSTRACT

Disclosed is a non-invasive technique for determining with high precision vascular disease, in particular arteriosclerosis, vascular stenosis, and aneurisms. This technique is achieved by a program that determines vascular disease in a subject by comparing normal distribution graphs obtained from a subject to normal distribution graphs obtained from a normal individual, which are based on reflective echo waveforms obtained by sending ultrasonic waves to the subject's pulsating blood vessels, detecting correlation or difference between the normal distribution graphs, and, if a difference in the normal distribution graphs is detected, implementing on the computer a step for determining that the subject has a vascular disease.

11 Claims, 19 Drawing Sheets

PROGRAM, MEDIUM, AND DEVICE FOR DETERMINING VASCULAR DISEASE

CROSS-REFERENCE TO RELATED APPLICATIONS

The present application claims priority from Japanese Patent Application No. 2010-159797 filed on Jul. 14, 2010. The entire contents of this application are incorporated herein by reference.

TECHNICAL FIELD

The present invention relates to programs, media, and devices for determining vascular disease in a subject, as well as to programs, media, and devices for evaluating the progress of arteriosclerosis in a subject.

BACKGROUND ART

Arteriosclerosis indicates a state in which arteries are thickened and hardened, leading to various pathological conditions. If narrowing of blood vessels occurs as arteriosclerosis becomes worse, the flow of blood in the arteries may be blocked, possibly causing fatal diseases such as cerebral infarction and myocardial infarction as oxygen and nutrients cannot reach critical tissues. In the case of arteriosclerosis, if artery walls become weakened due to atherosclerosis associated with large amounts of lipid deposition, vessel walls are expanded due to blood pressure, causing aneurysm. Rupture of aneurysm also can kill organisms.

If vascular diseases, such as arteriosclerosis, narrowing of blood vessels, and aneurysm, can be discovered at an early stage, it is possible to prevent fatal diseases, such as cerebral infarction and rupture of aneurysm, from occurring. In particular, aneurysm surgery is risky. Therefore, it is desirable that blood vessels be preserved as long as possible, and aneurysm be removed at a safe stage by surgery. Accordingly, noninvasive diagnosis is preferred for vascular diseases overall.

As a noninvasive diagnosis method for vascular diseases, the following methods are known. PWV is a method of evaluating the stiffness of blood vessels by measuring elastic-wave propagation speeds of the blood vessels (Refer to "Womersley J R: Oscillatory motion of a viscous liquid in a thin-walled elastic tube, I: The linear approximation for long waves. Phil Mag, 1955; 46:199-221" as Non-Patent Document 1; the contents of Non-Patent Document 1 are incorporated herein by reference.). IMT is a method of observing the shapes of vessel walls through imaging of blood vessels by ultrasonic waves (Refer to "Pignoli P, et al: Intimal plus medical thickness of the arterial wall: A direct measurement with ultrasound imaging. Circulation, 1986; 74: 1399-1406" as Non-Patent Document 2; the contents of Non-Patent Document 2 are incorporated herein by reference.). ABI is a method of examining blood-flow resistance by measuring a difference in blood pressure between two points (Refer to "Weiltz J I: Diagnosis and treatment of chronic arterial insufficiency of lower extremities, a critical review, AHA Medical/Scientific Sttements, 1996" as Non-Patent Document 3; the contents of Non-Patent Document 3 are incorporated herein by reference.).

DISCLOSURE OF THE INVENTION

Problems to be Solved by the Invention

However, the methods disclosed in the above Non-Patent Documents 1 to 3 each have problems. Deterioration in the strength of vessel walls cannot be determined only from the stiffness measured by PWV. Only with the shape of vessel walls observed by INT, it is difficult to evaluate a decrease in the strength of vessel walls. Since a correlation between the blood-flow resistance measured by ABI and vascular disease is poor, the method is not a direct examination method for vascular disease.

An object to be achieved by the present invention is to provide a method of determining vascular diseases, in particular arteriosclerosis, narrowing of blood vessels, and aneurysm, with a high degree of accuracy even though the method is noninvasive.

Means of Solving the Problems

To achieve the above object, the present inventors thought that, based on acceleration responsiveness of vessel walls by ultrasonic Doppler method, the progress of vascular disease could be noninvasively diagnosed as a viscoelasticity expression degree. As a result of extensive studies, the present inventors focused on vibration characteristics of the vessel walls detected during the diagnosis, and found that, as arteriosclerosis progresses, a vessel-wall vibration main waveform, represented by a norm distribution graph, overall moves to a lower frequency side, and that a peak of the waveform also moves to a lower frequency region. The present inventors decided to call the following mode f1 (also referred to as average mode): the mode in which a peak of vessel-wall vibration main waveform can be observed.

Moreover, the present inventors also found that, as aneurysm is expressed, a second wave waveform becomes expressed in a high-frequency region. The present inventors decided to call the following mode f2: the mode in which a peak of the second wave waveform can be observed. Furthermore, the present inventors observed that the high-frequency wave became obvious when aneurysm walls had a sufficient strength, and that the high-frequency wave disappeared when the strength of the aneurysm walls was weakened.

Meanwhile, it was found that entropy (S), which represents a correlation between progress of viscoelasticity and progress of arteriosclerosis that the present inventors have focused on, is correlated with f1.

The present inventors have succeeded in evaluating the progress of arteriosclerosis and aneurysm by using the intensity of f1 and f2. It was found that, by using the present invention, it is possible to instantaneously evaluate the possibility of vascular disease through computer analysis based on ultrasonic-wave diagnosis data; and that it is possible to determine vascular diseases, such as arteriosclerosis, narrowing of blood vessels, and aneurysm, with a high degree of accuracy. The present invention in one completed based on the above findings.

According to the present invention, what is provided is a program for determining vascular disease in a subject, wherein the program causes a computer to execute:

(1) a step of obtaining a wavelet spectrum by performing a discrete wavelet transform on a waveform of a reflected echo that is obtained by transmitting ultrasonic waves to beating blood vessels of a subject;

(2) a step of performing mode decomposition of the wavelet spectrum obtained by the step (1) to obtain a plurality of spectrums classified by mode;

(3) a step of performing an inverse wavelet transform on the plurality of classified-by-mode spectrums obtained by the step (2) to obtain a plurality of corresponding waveforms classified by mode;

(4) a step of calculating, from the plurality of classified-by-mode waveforms obtained by the step (3), a plurality of corresponding norm values;
(5) a step of outputting a norm distribution graph by plotting the plurality of norm values calculated by the step (4) for each of corresponding modes;
(6) a step of comparing the norm distribution graph output by the step (5) with a norm distribution graph obtained from a normal individual to detect that the norm distribution graphs match, or differ from, each other; and
(7) a step of determining that the subject has vascular disease in the case where a difference between the norm distribution graphs is detected by the step (6).

preferably, the vascular disease is arteriosclerosis, narrowing of blood vessels, or aneurysm.

Preferably, the vascular disease is arteriosclerosis, and the difference between the norm distribution graphs is a difference in f1, which is a mode in which a peak value on a norm distribution graph is observed.

Preferably, the vascular disease is aneurysm, and the difference between the norm distribution graphs is a difference in the number of peaks on a norm distribution graph.

According to another aspect of the present invention, what is provided is a program for evaluating progress of arteriosclerosis in a subject, wherein the program causes a computer to execute:
(a) a step of obtaining a wavelet spectrum by performing a discrete wavelet transform on a waveform of a reflected echo that is obtained by transmitting ultrasonic waves to beating blood vessels of a subject;
(b) a step of performing mode decomposition of the wavelet spectrum obtained by the step (a) to obtain a plurality of spectrums classified by mode;
(c) a step of performing an inverse wavelet transform on the plurality of classified-by-mode spectrums obtained by the step (b) to obtain a plurality of corresponding waveforms classified by mode;
(d) a step of calculating, from the plurality of classified-by-mode waveforms obtained by the step (c), a plurality of corresponding norm values;
(e) a step of outputting a norm distribution graph by plotting the plurality of norm values calculated by the step (d) for each of corresponding modes;
(f) a step of detecting f1, which is a mode in which a peak value is observed on the norm distribution graph output by the step (e);
(g) a step of constituting a two-dimensional attractor from a waveform of a reflected echo that is obtained by transmitting ultrasonic waves to beating blood vessels of a subject;
(h) a step of calculating entropy from a probability of a trajectory represented by the two-dimensional attractor constituted by the step (g);
(i) a step of outputting an entropy-average mode distribution graph that is obtained by plotting the entropy calculated by the step (h) to a mode around f1 detected by the step (f); and
(j) a step of comparing the entropy-average mode distribution graph output by the step (i) with an entropy-average mode distribution graph obtained from a normal individual, and evaluating the progress of arteriosclerosis in the subject based on how much the entropy increases.

According to another aspect of the present invention, what is provided is a computer-readable storage medium in which the program of the present invention is stored.

According to another aspect of the present invention, what is provided is a vascular disease determination device for determining vascular disease in a subject, the device including:

(1) means for obtaining a wavelet spectrum by performing a discrete wavelet transform on a waveform of a reflected echo that is obtained by transmitting ultrasonic waves to beating blood vessels of a subject;
(2) means for performing mode decomposition of the wavelet spectrum obtained by the means (1) to obtain a plurality of spectrums classified by mode;
(3) means for performing an inverse wavelet transform on the plurality of classified-by-mode spectrums obtained by the means (2) to obtain a plurality of corresponding waveforms classified by mode;
(4) means for calculating, from a plurality of classified-by-mode waveforms obtained by the means (3), a plurality of corresponding norm values;
(5) means for outputting a norm distribution graph by plotting the plurality of norm values calculated by the means (4) for each of corresponding modes;
(6) means for comparing the norm distribution graph output by the means (5) with a norm distribution graph obtained from a normal individual to detect that the norm distribution graphs match, or differ from, each other; and
(7) means for determining that the subject has vascular disease in the case where a difference between the norm distribution graphs is detected by the means (6).

According to another aspect of the present invention, what is provided is an arteriosclerosis progress evaluation device for evaluating progress of arteriosclerosis in a subject, the device including:
(a) means for obtaining a wavelet spectrum by performing a discrete wavelet transform on a waveform of a reflected echo that is obtained by transmitting ultrasonic waves to beating blood vessels of a subject;
(b) means for performing mode decomposition of the wavelet spectrum obtained by the means (a) to obtain a plurality of spectrums classified by mode;
(c) means for performing an inverse wavelet transform on the plurality of classified-by-mode spectrums obtained by the means (b) to obtain a plurality of corresponding waveforms classified by mode;
(d) means for calculating, from the plurality of classified-by-mode waveforms obtained by the means (c), a plurality of corresponding norm values;
(e) means for outputting a norm distribution graph by plotting the plurality of norm values calculated by the means (d) for each of corresponding modes;
(f) means for detecting f1, which is a mode in which a peak value is observed on the norm distribution graph output by the means (e);
(g) means for constituting a two-dimensional attractor from a waveform of a reflected echo that is obtained by transmitting ultrasonic waves to beating blood vessels of a subject;
(h) means for calculating entropy from a probability of a trajectory represented by the two-dimensional attractor constituted by the means (g);
(i) means for outputting an entropy-average mode distribution graph that is obtained by plotting the entropy calculated by the means (h) to a mode around f1 detected by the means (f); and
(j) means for comparing the entropy-average mode distribution graph output by the means (i) with an entropy-average mode distribution graph obtained from a normal individual, and evaluating the progress of arteriosclerosis in the subject based on how much the entropy increases.

Effects of the Invention

According to the program of the present invention, it is possible to noninvasively determine vascular disease, in particular arteriosclerosis, narrowing of blood vessels and aneurysm, from change characteristics of vessel-wall vibration frequency under pulsation. Moreover, a high-accuracy vascular vibration waveform can be obtained by reproducing the waveform of the frequency range thereof. Therefore, it is possible to reduce measurement error when the movement of vessel walls is measured. Accordingly, the program of the present invention can dramatically improve the accuracy of vascular disease determination.

The following findings have not been known so far: a finding about viscoelasticity of vessel walls associated with progress of arteriosclerosis; and a finding about a process of determining, from a change in the frequency characteristic of vessel-wall vibration, disturbance of vessel-wall vibration that results from disturbance of blood flow caused by the existence of aneurysm or narrowing of blood vessels. That is, the program of the present invention is the first to employ a method of associating the frequency characteristic of the vessel-wall acceleration responsiveness main waveform with the vessel-wall viscoelasticity expression degree, and also diagnosing a change in the geometry of aneurysm with the inclusive of a structural strength thereof. The program of the present invention has employed the above method, thereby enabling diagnosis of a decrease in stiffness associated with rupture of blood vessels. Moreover, it is possible to more accurately diagnose a correlation of organs with arteriosclerosis, as well as to diagnose how far vascular disease has spread. Thus, a device and method that use the program of the present invention are designed to directly detect a change in the mechanical property of vessel walls, aneurysm, and narrowing of blood vessels. The device and method can be a determination device or method that can noninvasively and directly diagnose vascular disease with the highest level of accuracy.

Conventional methods are indirect diagnosis methods for arteriosclerosis, such as pulse wave velocity (PWV) of vessel walls and changes in geometry (IMT). It is unclear whether the conventional methods are able to show original, actual conditions of arteriosclerosis. To the contrary, the program and device of the present invention are constituted to extract the vibration frequency in an inverse-problem manner by using digital filters and wavelet transform, and are able to eliminate most of measurement error. Therefore, the accuracy of determination achieved by the program and device is higher than ever before.

MODE FOR CARRYING OUT THE INVENTION

Hereinafter, the present invention will be described in detail.

A program of a first aspect of the present invention is a program that enables a computer to determine vascular disease in a subject, and includes the following steps:

(1) a step of obtaining a wavelet spectrum by performing a discrete wavelet transform on a waveform of a reflected echo that is obtained by transmitting ultrasonic waves to beating blood vessels of a subject;

(2) a step of performing mode decomposition of the wavelet spectrum obtained by the step (1) to obtain a plurality of spectrums classified by mode;

(3) a step of performing an inverse wavelet transform on the plurality of classified-by-mode spectrums obtained by the step (2) to obtain a plurality of corresponding waveforms classified by mode;

(4) a step of calculating, from the plurality of classified-by-mode waveforms obtained by the step (3), a plurality of corresponding norm values;

(5) a step of outputting a norm distribution graph by plotting the plurality of norm values calculated by the step (4) for each of corresponding modes;

(6) a step of comparing the norm distribution graph output by the step (5) with a norm distribution graph obtained from a normal individual to detect that the norm distribution graphs match, or differ from, each other; and (7) a step of determining that the subject has vascular disease in the case where a difference between the norm distribution graphs is detected by the step (6).

The vascular disease determined by the program of the first aspect of the present invention is not specifically restricted as long as the disease can be determined by the above procedure. However, the vascular disease is preferably arteriosclerosis, narrowing of blood vessels, or aneurysm.

Figure 1:
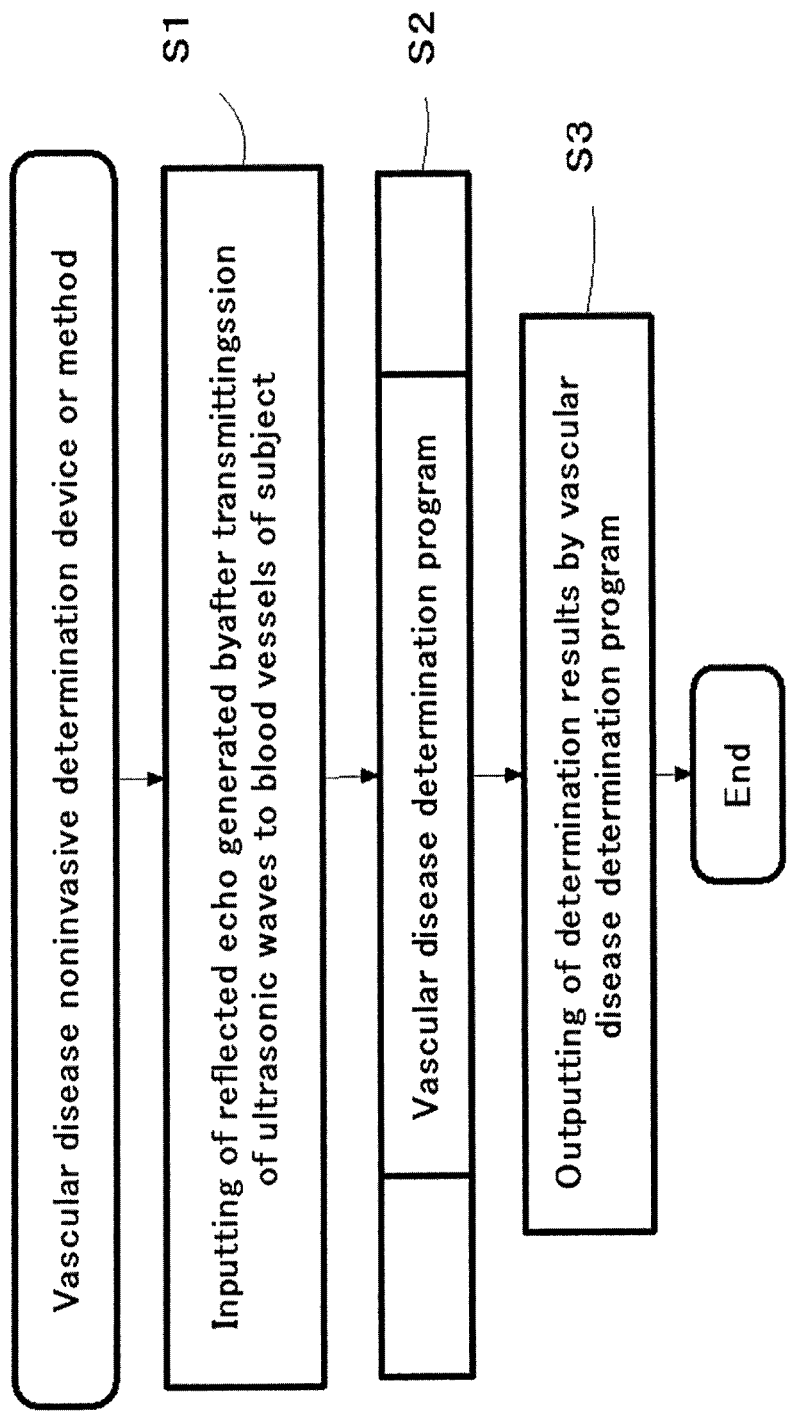
FIG. 1 is a diagram showing one example of a noninvasive determination device or method for vascular disease into which a program of the present invention is incorporated.

The program of the first aspect of the present invention (also referred to as a vascular disease determination program, hereinafter) is for example used as a vascular disease determination program (S2 of FIG. 1) in a vascular disease non-invasive determination device or method whose operating flow is shown in FIG. 1.

Figure 5:
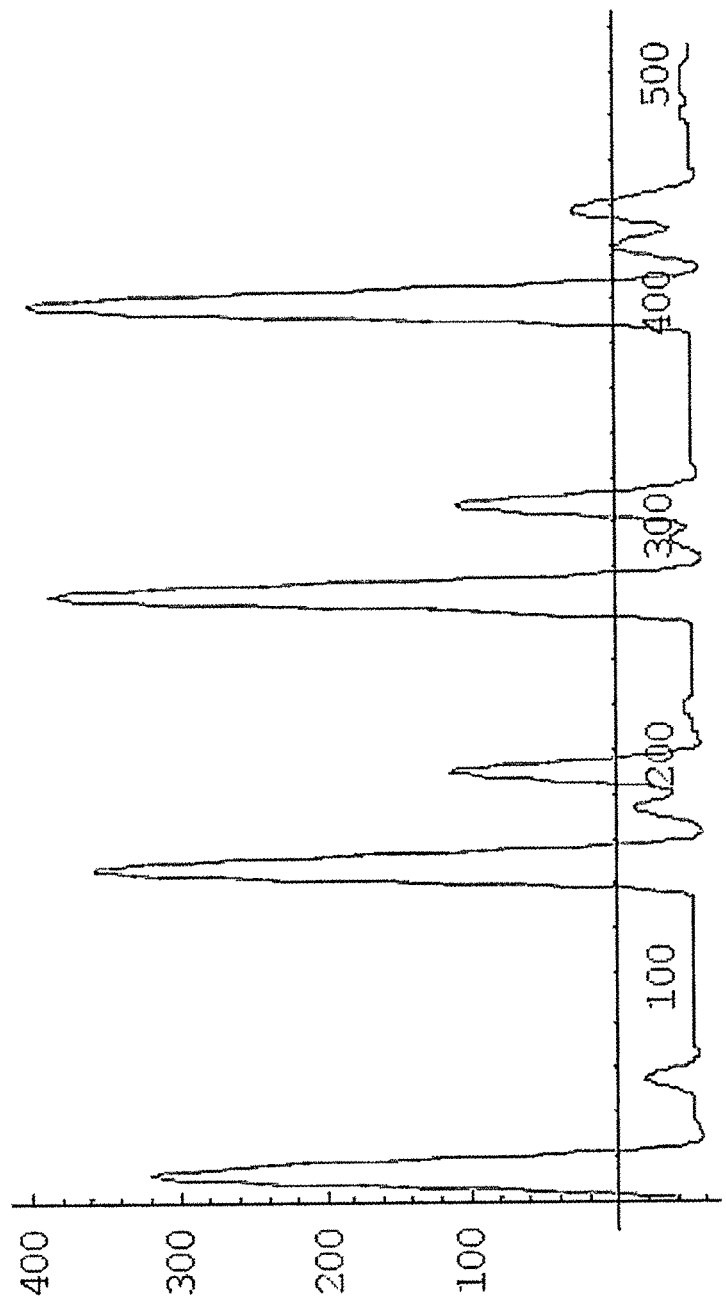
FIG. 5 is a diagram showing a waveform of a reflected echo that is obtained by vertically transmitting ultrasonic waves to beating blood vessels of a subject.

The vascular disease determination program of the present invention uses, as an input value, waveform information of a reflected echo that is obtained by transmitting ultrasonic waves to beating blood vessels of a subject (S1 of FIG. 1). As for a method of transmitting ultrasonic waves to blood vessels of a subject, already-known methods may be employed. It is preferred that ultrasonic waves be vertically transmitted, or at 90 degrees with respect to the blood vessels of the subject. A method of obtaining the reflected echo is not specifically restricted as long as vibration frequencies of vessel walls can be selectively extracted. For example, if a digital filter method is employed, it is possible to extract only a signal of specific frequency or to reduce noise contained in signals at a time when ultrasonic waves are transmitted at an angle of 90 degrees or any other angle with respect to the blood vessels of the subject. The waveform of the reflected echo can be obtained by ultrasonic Doppler method with the use of devices disclosed in Japanese Unexamined Application Patent Publication (KOKAI) No. Hei5-23335 and "Acoustical imaging and processing of blood vessel and the related materials using ultrasound doppler effect" (Yokobori et al., Bio-Medical Materials and Engineering, Vol. 1, pp. 127-136, 1991) (the contents of the documents are incorporated herein by reference.). More specifically, to the blood vessel walls that are expanding and contracting, or to the beating blood vessel walls of the subject, ultrasonic waves of frequency f are transmitted in the vertical direction. From the blood vessel walls, the reflected echo whose frequency is changed to $f_0$ due to Doppler effect is received and obtained. The reflected echo thus obtained has a waveform shown in FIG. 5, for example.

According to the vascular disease determination program of the present invention, by sequentially subjecting the waveform of the reflected echo as an input value to mathematical processes, it is possible to finally determine whether or not the subject has vascular disease. For example, if the determination device shown in FIG. 1 has a display unit, the determination results may be displayed on the display unit (S3 of FIG. 1).

Figure 2:
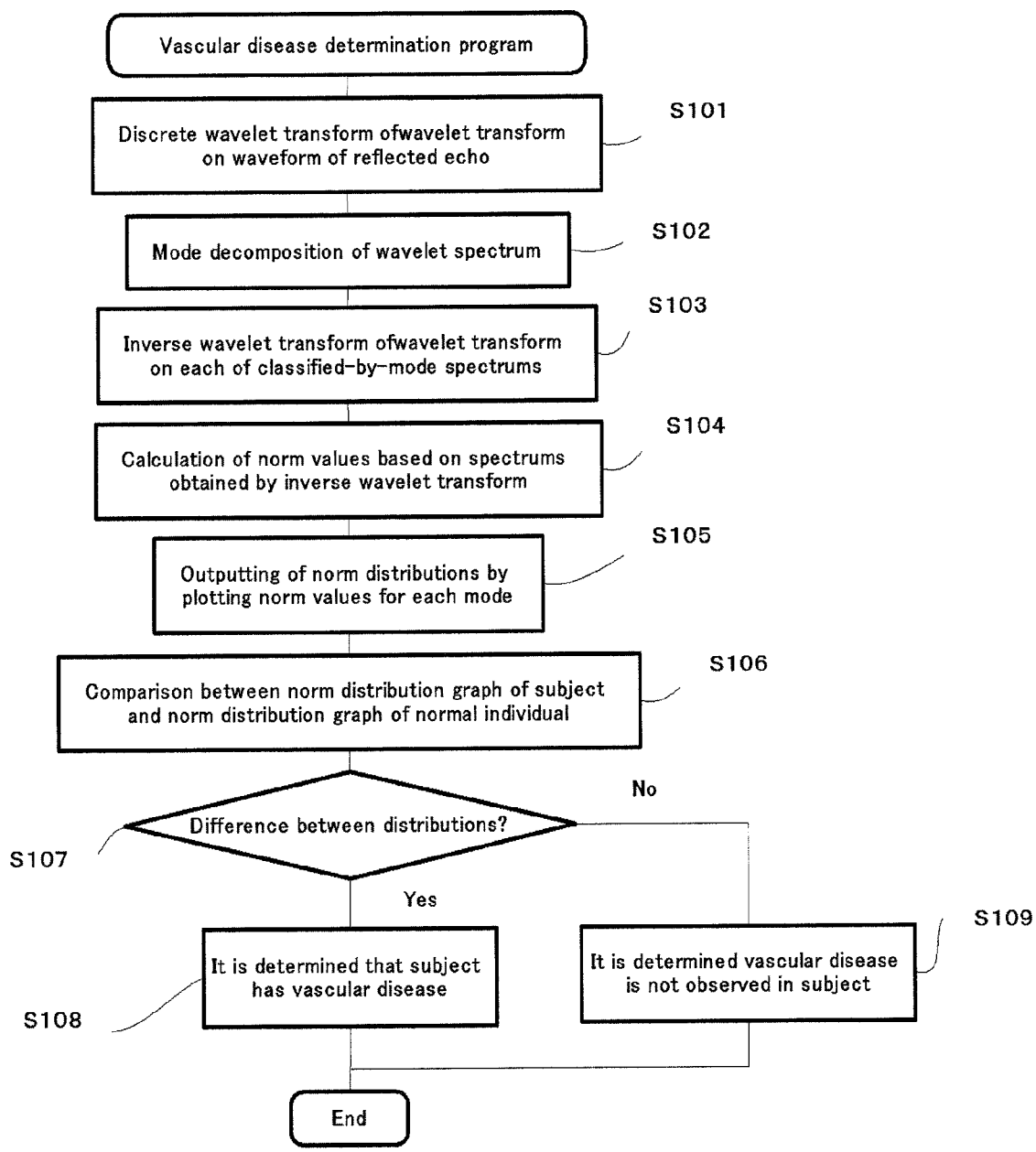
FIG. 2 is a diagram showing an embodiment of a process procedure of a vascular disease determination program of the present invention.
Figure 6:
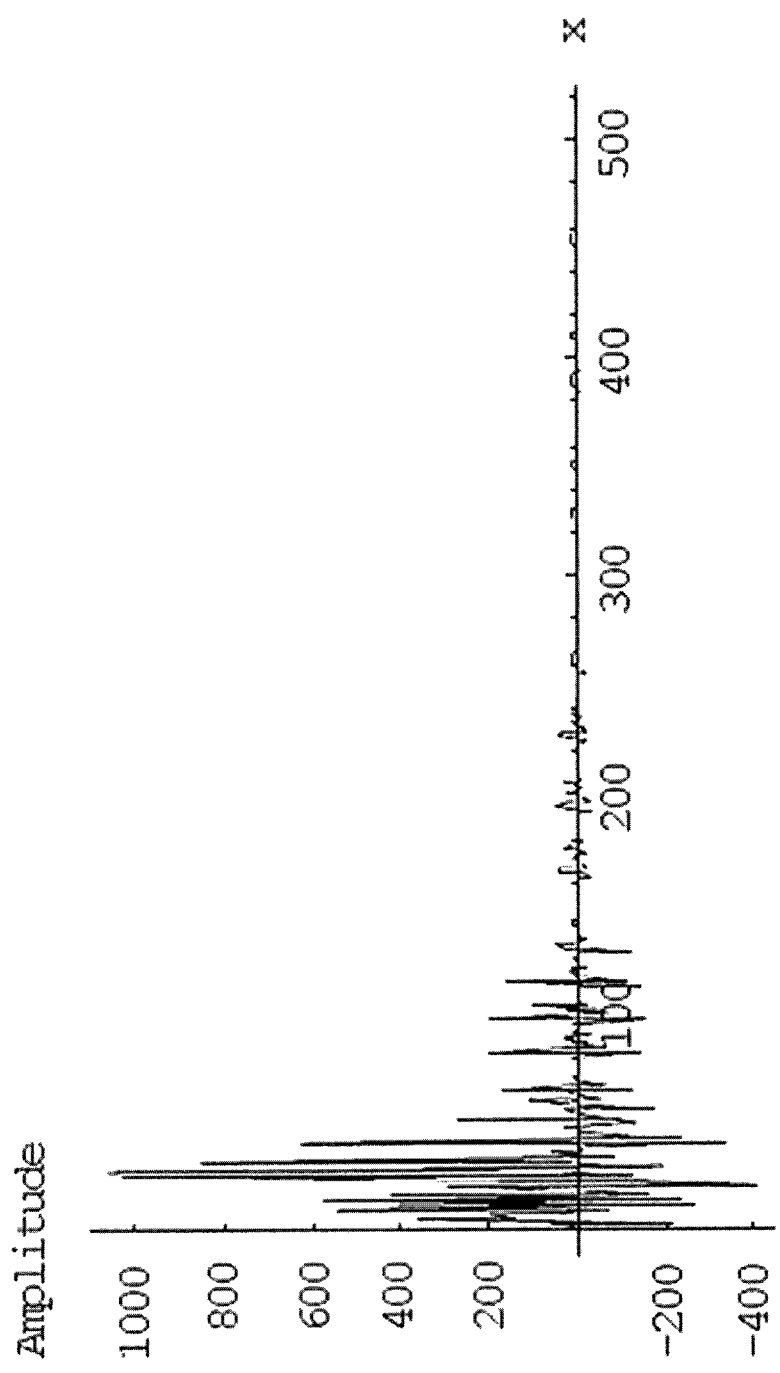
FIG. 6 is a diagram showing a wavelet spectrum that is obtained by discrete wavelet transform on the waveform of FIG. 5.

An embodiment of the process procedure of the vascular disease determination program of the present invention is shown in a flowchart of FIG. 2. A discrete wavelet transform is carried out by multiplying waveform vectors of the reflected echo that is obtained from the subject by a wavelet transform matrix to obtain a wavelet spectrum (S101 of FIG. 2). For example, FIG. 6 shows the wavelet spectrum that is obtained by performing a discrete wavelet transform on the waveform of the reflected echo shown in FIG. 5.

Figure 7:
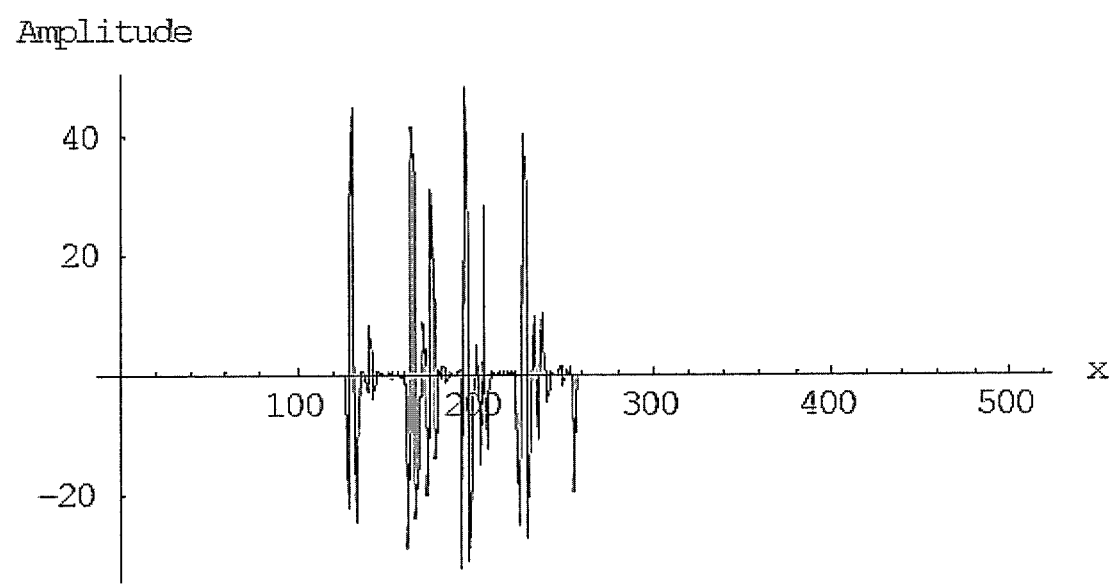
FIG. 7 is a diagram showing a spectrum of mode 6, among those obtained by mode decomposition of the spectrum of FIG. 6.

The mode decomposition of the wavelet spectrum that is obtained as described above is carried out to obtain a plurality of spectrums that are classified by mode (S102 of FIG. 2). For example, the wavelet spectrum shown in FIG. 6 may be mode-decomposed into eight modes as shown in Table 1 below. Among those thus obtained, a spectrum of mode 6 (Elements 65 to 128) is shown in FIG. 7.

TABLE 1

| Mode | Left element |
|------|--------------|
| 1    | 3 to 4       |
| 2    | 5 to 8       |
| 3    | 9 to 16      |
| 4    | 17 to 32     |
| 5    | 33 to 64     |
| 6    | 65 to 128    |
| 7    | 129 to 256   |
| 8    | 257 to 512   |

Figure 8:
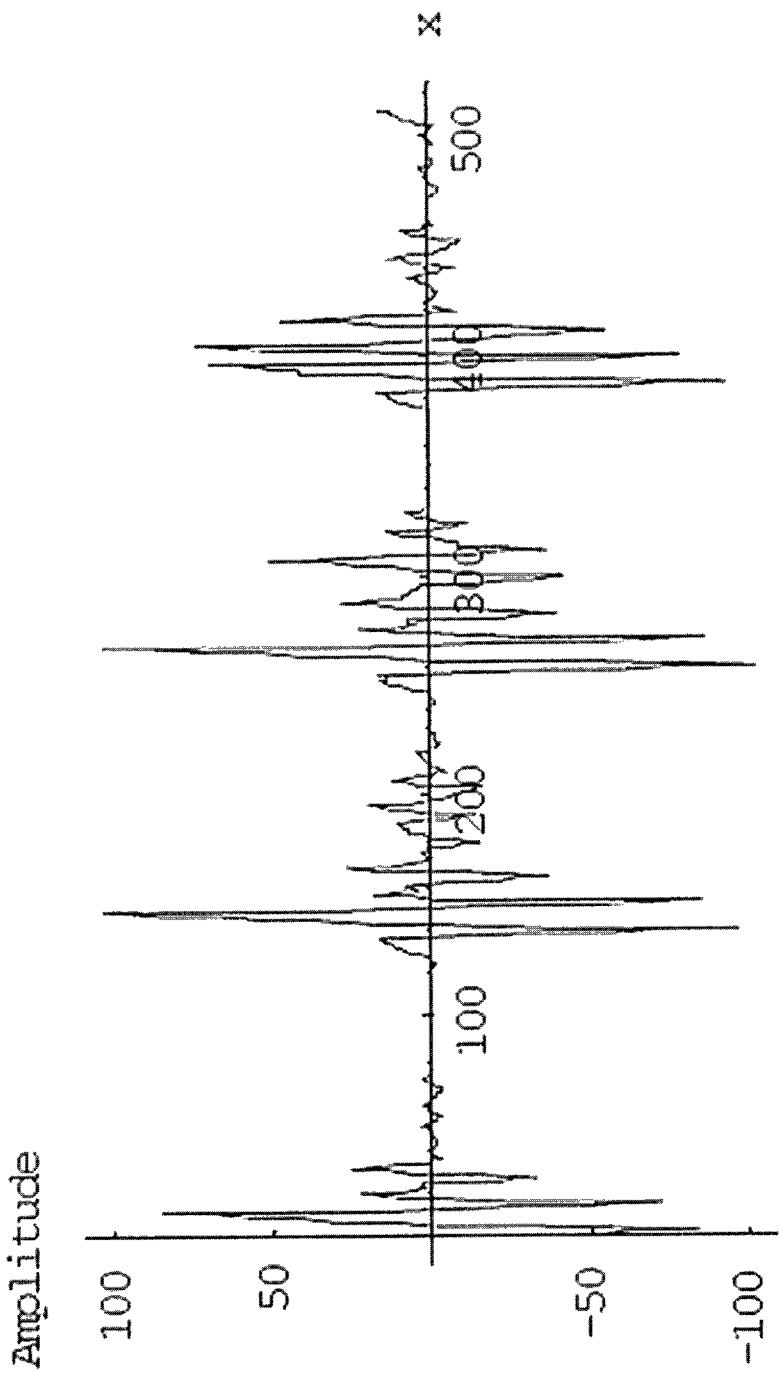
FIG. 8 is a diagram showing a spectrum that is obtained by inverse wavelet transform on the spectrum of FIG. 7.

An inverse wavelet transform is carried out by multiplying each of the plurality of classified-by-mode spectrums that are obtained as described above by the inverse of the wavelet transform matrix to obtain a plurality of corresponding waveforms that are classified by mode (S103 of FIG. 2). For example, FIG. 8 shows the waveform that is obtained by performing the inverse wavelet transform on the spectrum of mode 6, which is shown in FIG. 7.

Norm values are calculated for each of the plurality of classified-by-mode waveforms that are obtained as described above (S104 of FIG. 2). As for the norm values, if a vector of a waveform of mode m is represented by $$\vec{X}_m = (x_1, x_2, x_3, \ldots, x_n)^T \quad \text{[Formula 1]}$$

Figure 9:
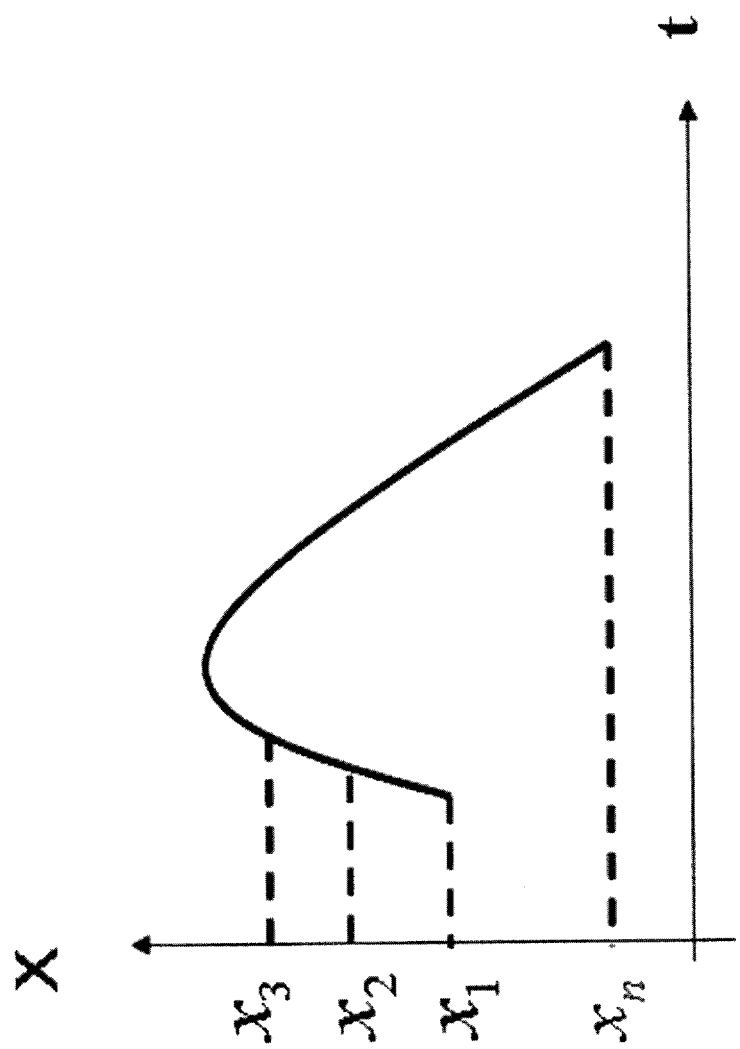
FIG. 9 is a conceptual diagram of norm distribution.

(wherein T represents time; refer to FIG. 9 for the meaning of division point x), then the norm value of mode m is defined as $$N_m = \sqrt{x_1^2 + x_2^2 + x_3^2 + \ldots + x_m^n} \quad \text{[Formula 2]}$$

For each of the modes that are decomposed by wavelet transform, a norm value of each mode, which is calculated from division point xi (i=1 to n) of a vibration waveform thereof, is calculated. Then, the distribution thereof is determined. In addition, the mode with the largest norm is regarded as main waveform frequency f1.

The relationship between the norm value and f1 is represented by the following formula with the use of Nm, which is defined as described above:

$$f_1 = \sum_{m=1}^{S} m N_m \quad \text{[Formula 3]}$$

In accordance with the procedure as described above, a wavelet transform on a reflected echo, which is on a time axis and is obtained by transmitting ultrasonic waves to beating blood vessels of a subject, is performed to obtain a wavelet spectrum that is on a frequency axis. Then, the mode decomposition of the wavelet spectrum is carried out to obtain spectrums that are classified by mode. After that, an inverse wavelet transform is performed to obtain waveforms that are on the time axis and are classified by mode. Then, norm values are calculated. As a result, norm values are obtained for each mode.

Figure 10:
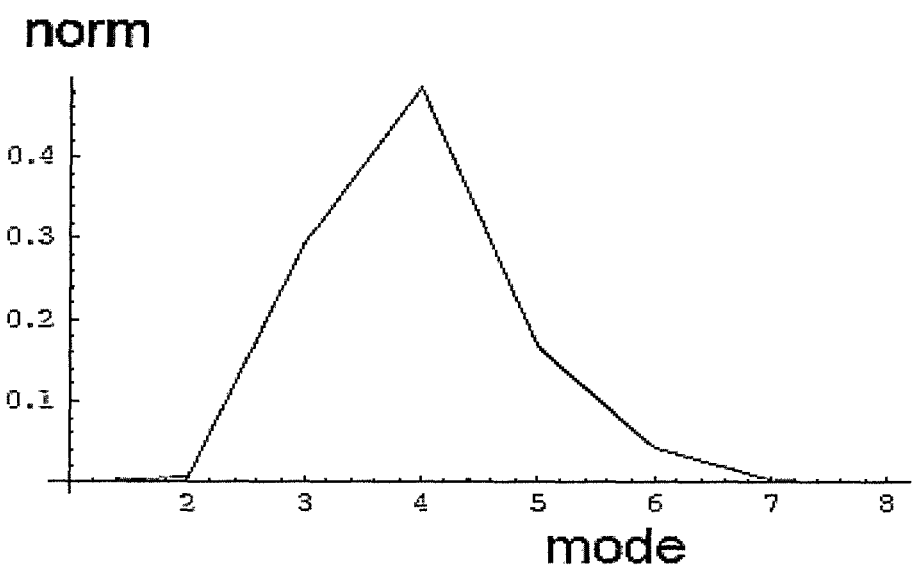
FIG. 10 is a diagram showing a norm distribution graph that is obtained from healthy people.
Figure 11:
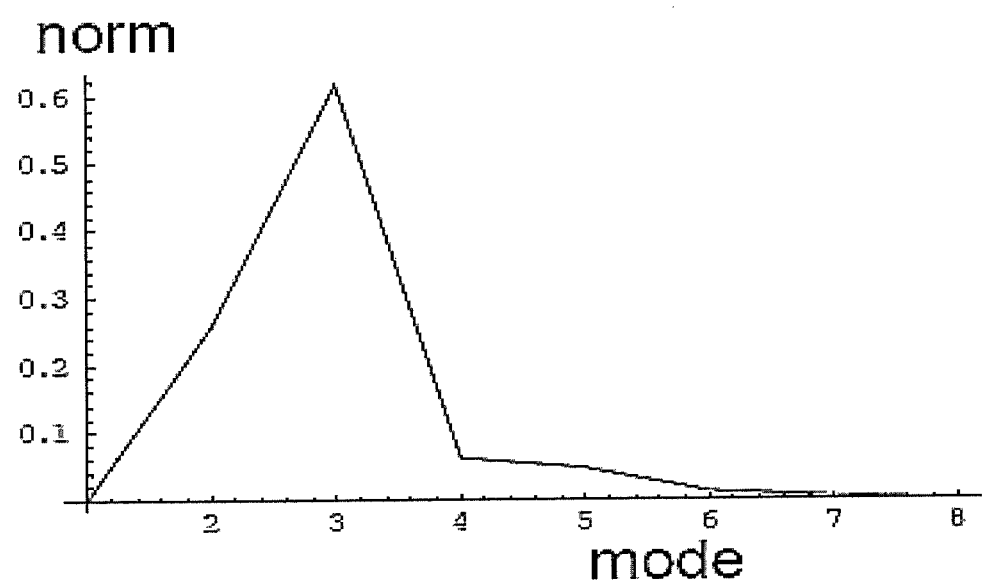
FIG. 11 is a diagram showing a norm distribution graph that is obtained from people suffering from arteriosclerosis.

A norm distribution graph is output by plotting the norm values, which are obtained as described above, on a y-axis, and modes on an x-axis (S105 of FIG. 2). The norm distribution graph of the subject, which is thus obtained, is compared with a norm distribution graph obtained from a normal individual in the same manner (S106 of FIG. 2) to detect whether the norm distribution graphs match, or differ from, each other (S107 of FIG. 2). For example, FIG. 10 shows a norm distribution graph obtained from healthy people, while FIG. 11 shows a norm distribution graph obtained from people suffering from arteriosclerosis. It is clear from FIGS. 10 and 11 that both overall have different distributions of norm values with respect to modes. In particular, both are different in f1, which is a mode in which peak norm values are observed. As shown in FIG. 11, the peak of the norm distribution graph that is obtained from people suffering from arteriosclerosis tends to be closer to a lower mode side (lower frequency side) than that of healthy people.

Accordingly, if the norm distribution graph obtained from the subject is compared with a norm distribution graph obtained from a normal individual, it is determined that the subject has arteriosclerosis at a time when a difference in f1 is detected, or preferably when f1 of the norm distribution graph obtained from the subject is closer to the lower frequency side than f1 of the norm distribution graph obtained from the normal individual, or more preferably when f1 of the norm distribution graph obtained from the subject is less than 4 (S107 of FIG. 2).

If the norm distribution graph obtained from the subject matches a norm distribution graph obtained from a normal individual, or if no difference is detected between the two, it is determined that vascular disease is not observed in the subject (S108 of FIG. 2). The determination results may be qualitative ones, such as whether or not a specific vascular disease exists, or may be quantitative ones, such as incidence of a specific vascular disease.

Figure 12:
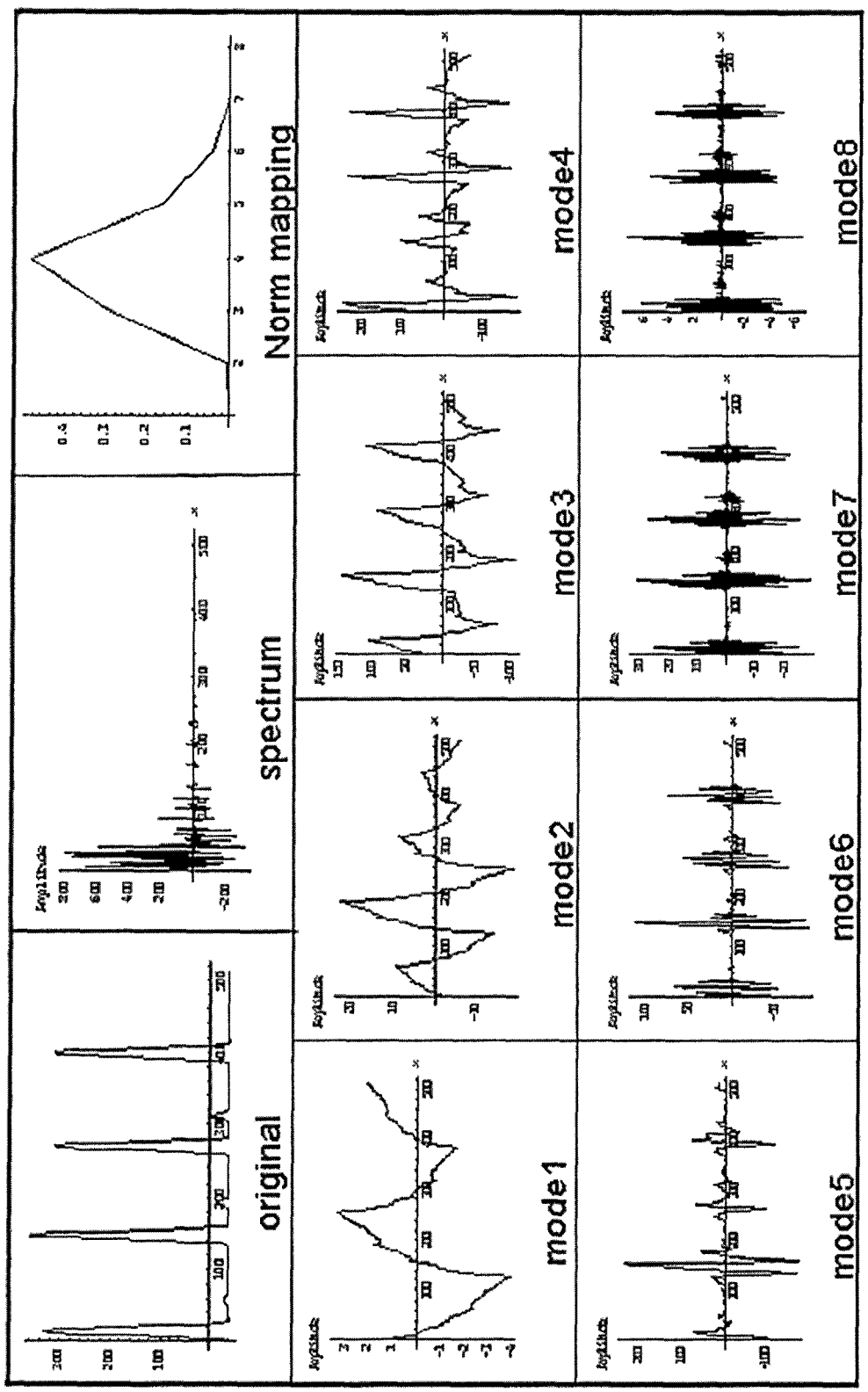
FIG. 12 is a diagram showing one example of waveform of reflected echo, wavelet spectrum, waveforms classified by mode, and norm distribution graph, which are obtained from healthy people.

FIG. 12 shows an embodiment of a series of graphs including those of wavelet spectrums and classified-by-mode waveforms, and norm distribution graphs, which are obtained from the waveform of a reflected echo obtained by transmitting ultrasonic waves to beating blood vessels of a healthy person in accordance with the above procedure.

Figure 13:
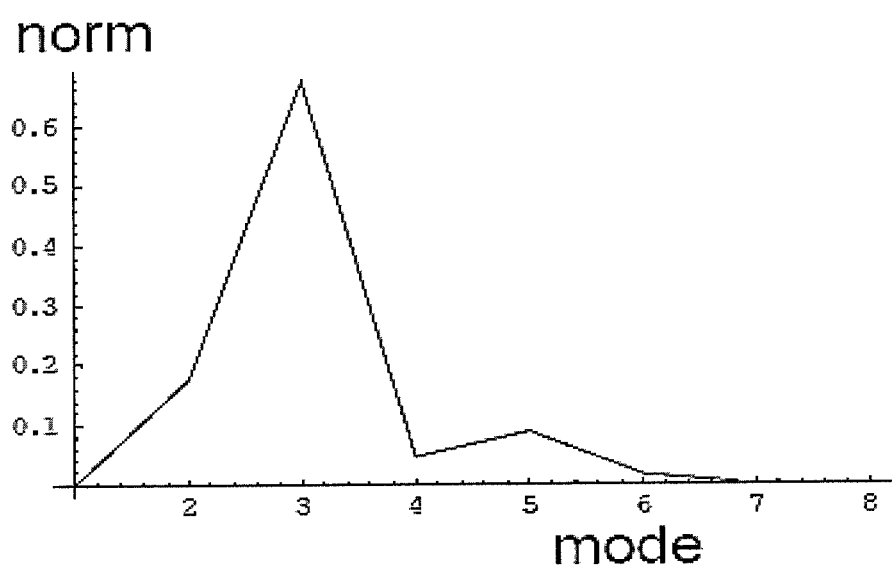
FIG. 13 is a diagram showing a norm distribution graph that is obtained from people suffering from aneurysm.

FIG. 13 shows one example of a norm distribution graph that is obtained from people suffering from aneurysm. As shown in FIG. 13, the norm distribution graph that is obtained from people suffering from aneurysm has two peaks. Incidentally, in the case where two peaks are obtained on a norm distribution graph, a peak of a relatively large norm value is called the "first peak," and a peak of a smaller norm value the "second peak."

The second peak as shown in FIG. 13 is not confirmed in a norm distribution graph obtained from a normal individual or from people suffering only from arteriosclerosis. The second peak is observed in a high-frequency side's mode, or around mode 5 for example, on a norm distribution graph obtained from people suffering from aneurysm and severe arteriosclerosis. Accordingly, if the norm distribution graph obtained from the subject is compared with a norm distribution graph obtained from a normal individual, it is determined that the subject has aneurysm at a time when a difference in the number of peaks is detected, or preferably when two or more peaks are detected on the norm distribution graph obtained from the subject, or more preferably when the second peak is detected at the high frequency side, or around mode 5 for example, of the norm distribution graph obtained from the subject.

Figure 14:
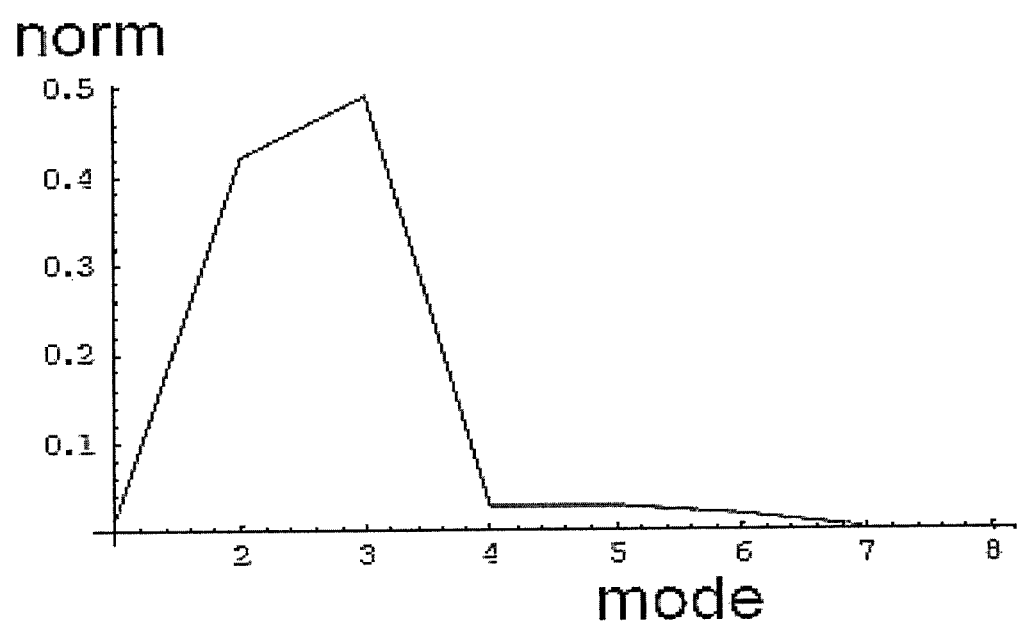
FIG. 14 is a diagram showing one example of a norm distribution graph that is obtained from people suffering from aneurysm and moderate arteriosclerosis.

FIG. 14 shows one example of a norm distribution graph that is obtained from people suffering from aneurysm and moderate arteriosclerosis. As shown in FIG. 14, from the norm distribution graph obtained from people whose arteriosclerosis has progressed, the second peak at the high frequency side has disappeared. As a result, the waveform which results from overlapping of two peaks is detected at a lower frequency side, or around modes 2 to 4 for example.

Figure 15:
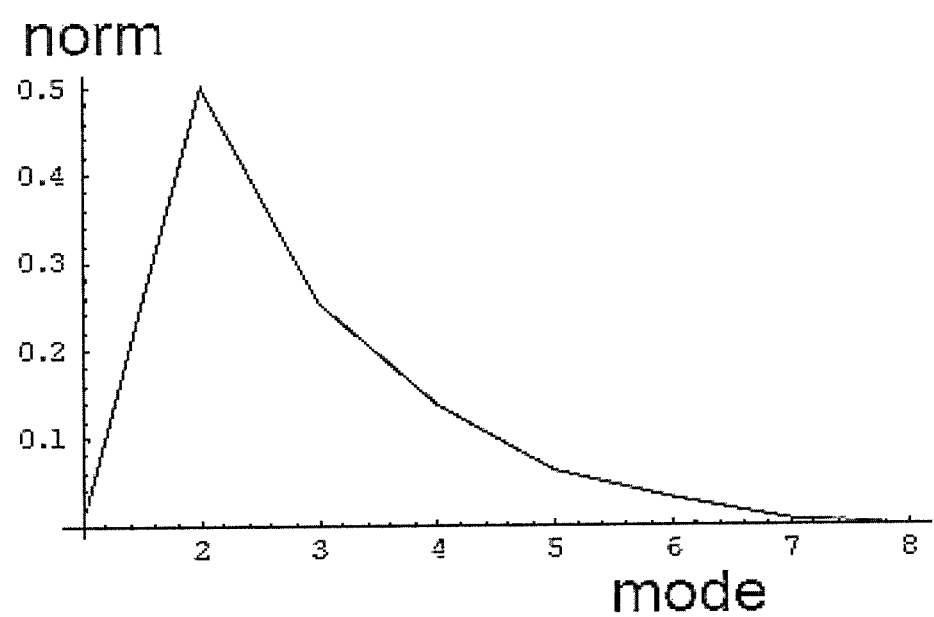
FIG. 15 is a diagram showing one example of a norm distribution graph that is obtained from people suffering from aneurysm and severe arteriosclerosis.

FIG. 15 shows one example of a norm distribution graph that is obtained from people suffering from aneurysm and severe arteriosclerosis. As shown in FIG. 15, as arteriosclerosis further progresses from moderate, it is not possible to distinguish between the first peak and the second peak. The first and second peaks are detected as one peak that is closer to a lower frequency side than a mode of a peak value of a norm distribution graph obtained from people suffering from mild arteriosclerosis, or as one peak around mode 2 for example.

Accordingly, if the norm distribution graph obtained from the subject has peaks in which two peaks overlap with each other at a lower frequency side, or preferably around modes 2 to 4, it is determined that the subject has aneurysm and moderate arteriosclerosis. If the norm distribution graph obtained from the subject has peaks that are closer to a lower frequency side than a mode of a peak value of a norm distribution graph obtained from people suffering from mild arteriosclerosis, or preferably has peaks around mode 2, it is determined that the subject has aneurysm and severe arteriosclerosis.

A program of a second aspect of the present invention is a program that enables a computer to evaluate progress of arteriosclerosis in a subject, and includes the following steps:

(a) a step of obtaining a wavelet spectrum by performing a discrete wavelet transform on a waveform of a reflected echo that is obtained by transmitting ultrasonic waves to beating blood vessels of a subject;

(b) a step of performing mode decomposition of the wavelet spectrum obtained by the step (a) to obtain a plurality of spectrums classified by mode;

(c) a step of performing an inverse wavelet transform on the plurality of classified-by-mode spectrums obtained by the step (b) to obtain a plurality of corresponding waveforms classified by mode;

(d) a step of calculating, from the plurality of classified-by-mode waveforms obtained by the step (c), a plurality of corresponding norm values;

(e) a step of outputting a norm distribution graph by plotting the plurality of norm values calculated by the step (d) for each of corresponding modes;

(f) a step of detecting f1, which is a mode in which a peak value is observed on the norm distribution graph output by the step (e);

(g) a step of constituting a two-dimensional attractor from a waveform of a reflected echo that is obtained by transmitting ultrasonic waves to beating blood vessels of a subject;

(h) a step of calculating entropy from a probability of a trajectory represented by the two-dimensional attractor constituted by the step (g);

(i) a step of outputting an entropy-average mode distribution graph that is obtained by plotting the entropy calculated by the step (h) to a mode around f1 detected by the step (f); and (j) a step of comparing the entropy-average mode distribution graph output by the step (i) with an entropy-average mode distribution graph obtained from a normal individual, and evaluating the progress of arteriosclerosis in the subject based on how much the entropy increases.

Figure 3:
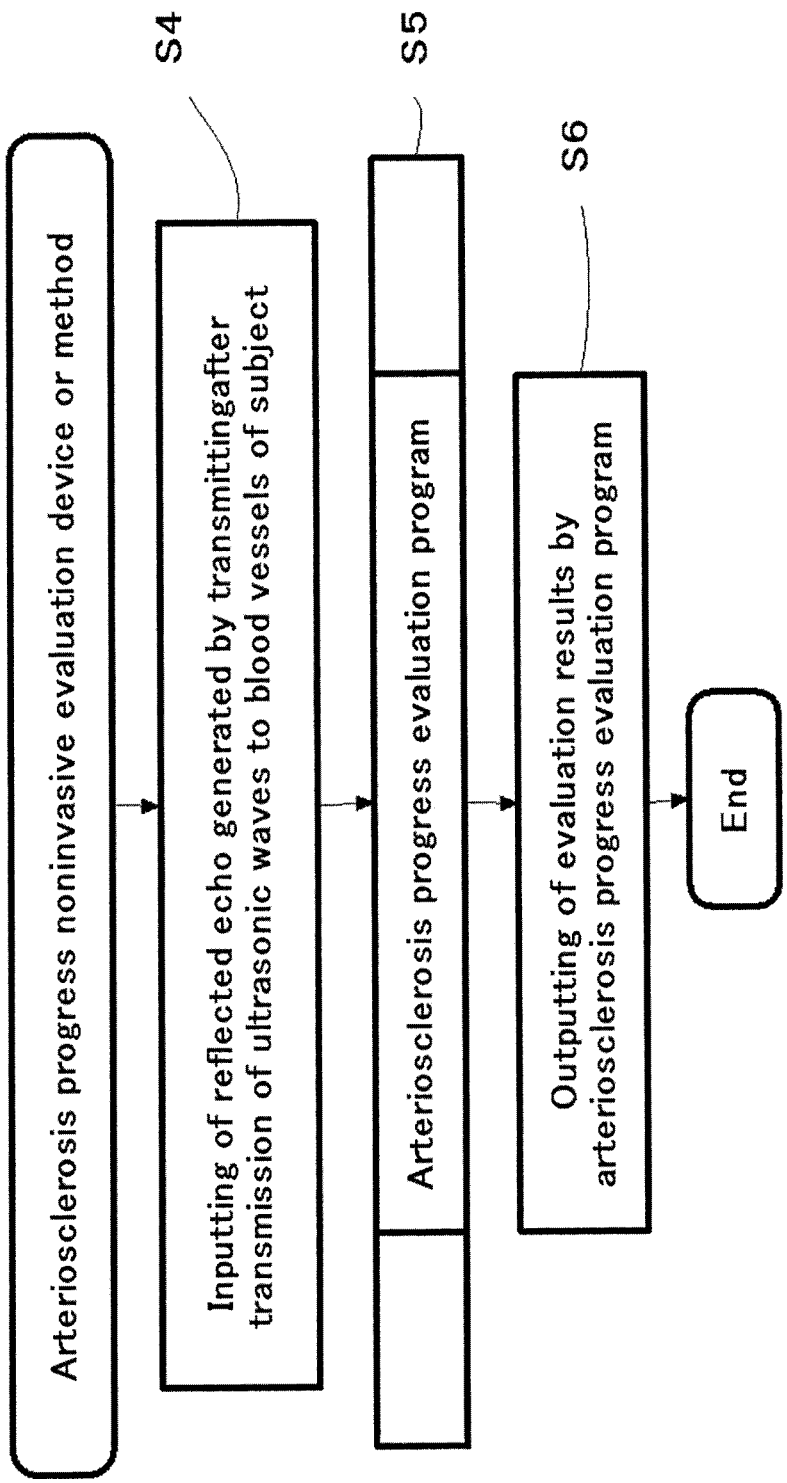
FIG. 3 is a diagram showing one example of a noninvasive evaluation device or method for progress of arteriosclerosis into which a program of the present invention is incorporated.

The program of the second aspect of the present invention (also referred to as an arteriosclerosis progress evaluation program, hereinafter) is used as an arteriosclerosis progress evaluation program (S5 of FIG. 3) in an arteriosclerosis progress noninvasive evaluation device or method whose operating flow is shown in FIG. 3, for example.

As in the case of the vascular disease determination program of the present invention, the arteriosclerosis progress evaluation program of the present invention uses, as an input value, waveform information of a reflected echo that is obtained by transmitting ultrasonic waves to beating blood vessels of a subject, or preferably transmitting ultrasonic waves at an angle of 90 degrees with respect to blood vessels of a subject (S4 of FIG. 3). According to the arteriosclerosis progress evaluation program of the present invention, by sequentially subjecting the waveform of the reflected echo, which is obtained by transmitting ultrasonic waves to the blood vessels of the subject, as an input value to mathematical processes, it is possible to finally evaluate the progress of arteriosclerosis in the subject (S5 of FIG. 3). For example, if the determination device shown in FIG. 3 has a display unit, the determination results may be displayed on the display unit (S6 of FIG. 3).

Figure 4:
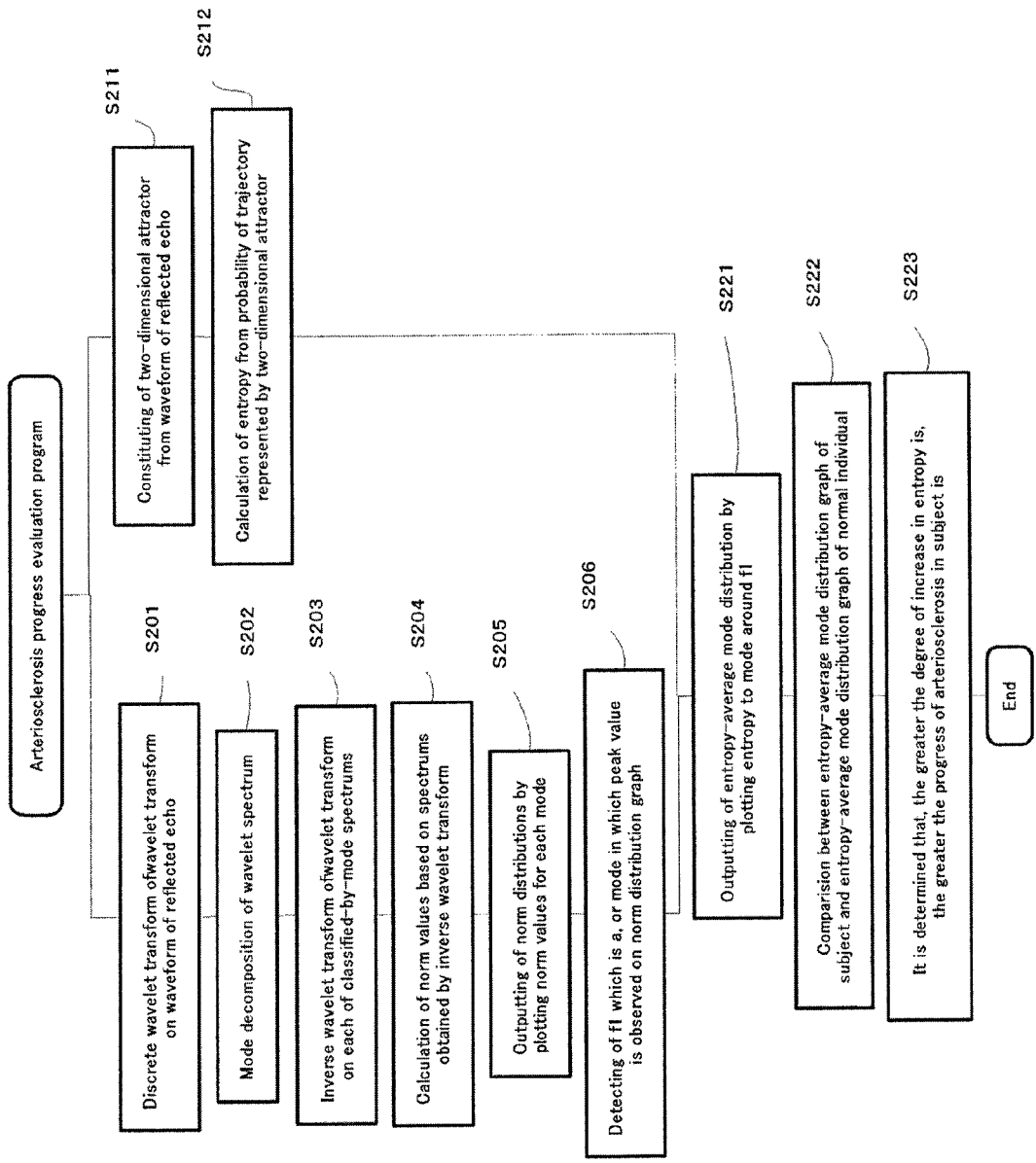
FIG. 4 is a diagram showing an embodiment of a process procedure of an arteriosclerosis progress evaluation program of the present invention.

An embodiment of the process procedure of the arteriosclerosis progress evaluation program of the present invention is shown in a flowchart of FIG. 4. S201 to S205 of the flowchart of FIG. 4 correspond to S101 to S205 of the flowchart of FIG. 2.

According to the arteriosclerosis progress evaluation program of the present invention, on a norm distribution graph obtained from the subject, f1, which is a mode in which a peak value is observed, is detected (S206 of FIG. 4). As described above, f1 of a norm distribution graph obtained from people suffering from arteriosclerosis is detected closer to a lower frequency side than f1 of a norm distribution graph obtained from a normal individual, or is detected at less than 4 for example.

Figure 16:
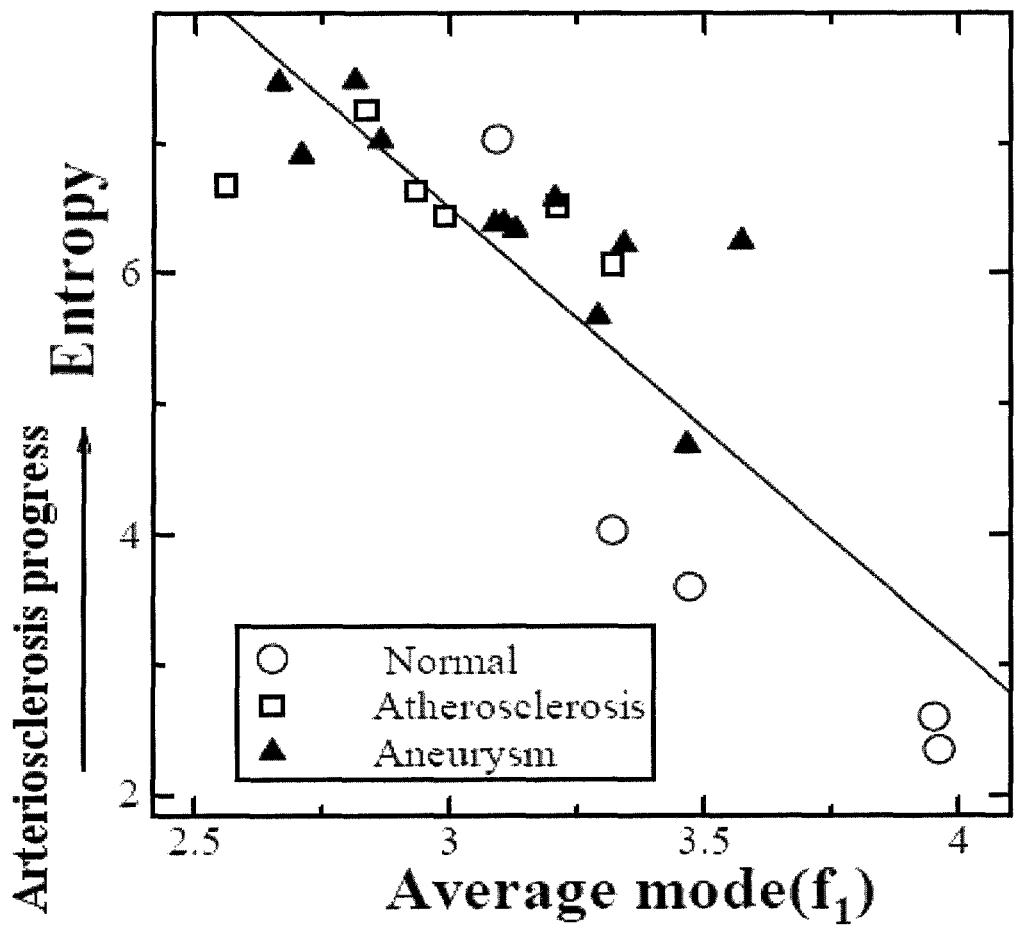
FIG. 16 is a diagram showing an entropy-average mode distribution graph that is obtained from healthy people (○), people suffering from arteriosclerosis (□), and people suffering from aneurysm (▲).

The arteriosclerosis progress evaluation program of the present invention is designed to evaluate the progress of arteriosclerosis based on an entropy-average mode distribution in which entropy is plotted for f1 that is thus obtained. The entropy of each mode is calculated by constituting a two-dimensional attractor from a waveform of a reflected echo that is obtained by transmitting ultrasonic waves to beating blood vessels of a subject, and then using a probability of a trajectory represented by the two-dimensional attractor constituted (S211 and S212 of FIG. 4). The formation of the two-dimensional attractor and the calculation of entropy can be realized by referring to: "Analyses of the Unstable Behavior of Blood Vessels with Atherosclerosis and Aneurysm Based on the Chaos Theory" (pp. 169-171) and "The Analysis of Entropy for Dynamic Behavior of the Blood Vessel Wall" (pp. 171-173) of "The Analysis and Diagnosis of Unstable Behavior of the Blood Vessel Wall with an Aneurysm Based on Noise Science" (Yokobori et al., Journal of Atherosclerosis and Thrombosis, Vol. 13, No. 4, pp. 163-174, 2006) (The contents of the document are incorporated herein by reference.).

by plotting the entropy thus calculated on a y-axis, and the average modes on an x-axis, the entropy is plotted with respect to the average modes, and a resultant entropy-average mode distribution graph is output (S221 of FIG. 4). FIG. 16 shows an embodiment of the entropy-average mode distribution graph. In FIG. 16, there is a correlation between f1 and entropy, with a correlation coefficient of 0.82. It is said that, in the case of a program that realizes PWV as described in Non-Patent Document 1, there is a correlation between output values, and healthy people, people suffering from arteriosclerosis and people suffering from aneurysm, with a correlation coefficient of 0.3 to 0.5. Therefore, the arteriosclerosis progress evaluation program of the present invention can appropriately evaluate the progress of arteriosclerosis compared with conventional programs.

As shown in FIG. 16, the entropy values for average modes of people suffering from arteriosclerosis (□) and of people suffering from aneurysm (▲) are higher than those of normal individuals (○). The degree thereof depends on how far arteriosclerosis has progressed. Accordingly, if the entropy-average mode distribution graph obtained from the subject is compared with an entropy-average mode distribution graph obtained from a normal individual (S222 of FIG. 4), it can be determined that, the greater the degree of increase in entropy is, the greater the progress of arteriosclerosis in the subject is (S223 of FIG. 4). The degree of increase in entropy may be detected by comparing maximum and/or minimum entropy values on the entropy-average mode distribution graphs, for example.

Moreover, a frequency analysis to which the program of the present invention is applied is able to determine aneurysm and evaluate progress of arteriosclerosis with a high level of accuracy. The frequency analysis can be performed through a procedure described below, for example.

Figure 17:
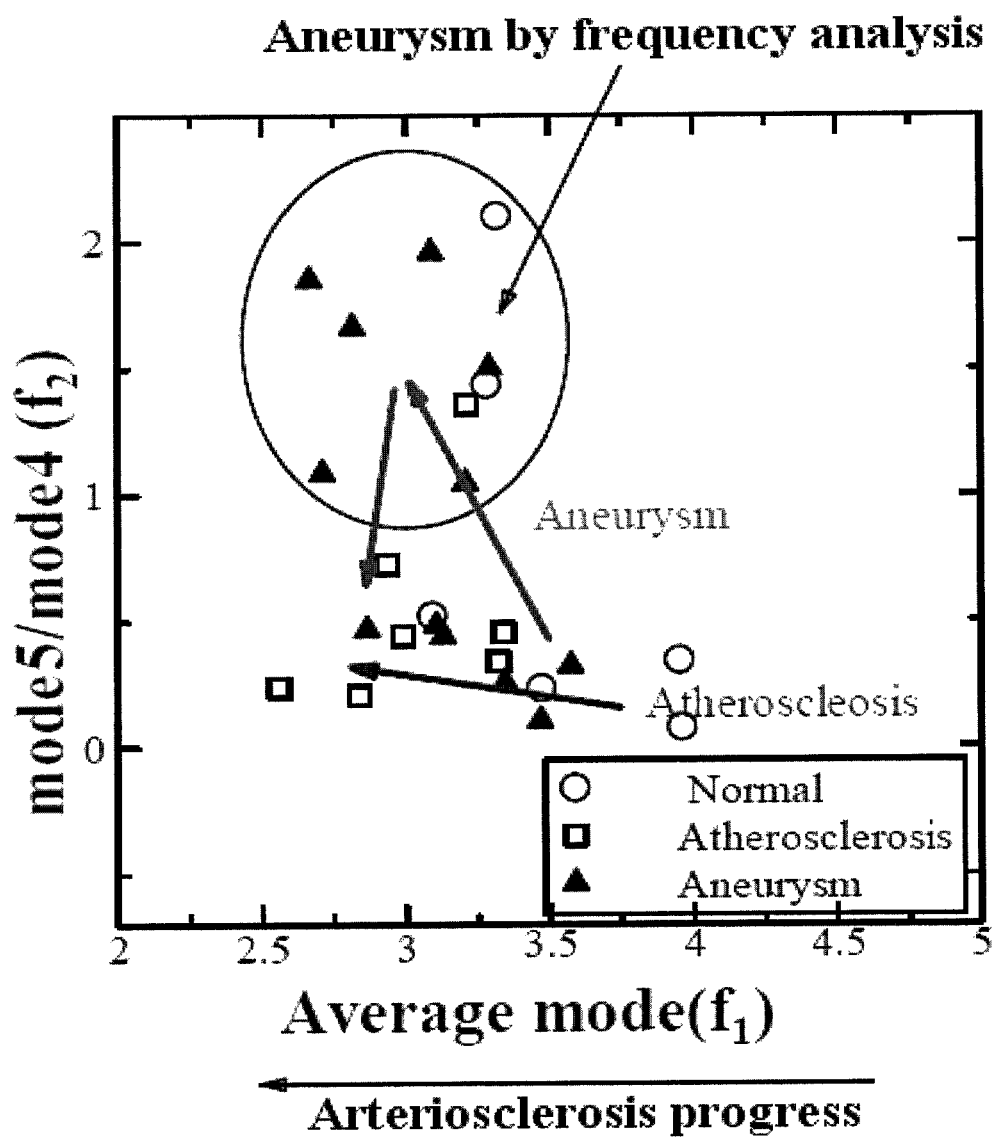
FIG. 17 is a diagram showing an f2 value-average mode distribution graph that is obtained from healthy people (○), people suffering from arteriosclerosis (□), and people suffering from aneurysm (▲).

In accordance with the procedure described above, from a norm distribution graph obtained from a subject, a mode in which the second peak is observed (also referred to as a second peak mode, hereinafter) is detected. A ratio value (Second peak norm value/Adjacent mode norm value) (also referred to as an "f2 value," hereinafter) is calculated by dividing the second peak norm value by the adjacent mode norm value. The obtained f2 value is plotted with respect to the average mode (f1). In this manner, a frequency analysis graph can be prepared. If there is aneurysm, the f2 value increases around average mode 3. Accordingly, if the f2 value is greater than or equal to 1 preferably at average mode 3, the subject may be highly likely to suffer from aneurysm. FIG. 17 is a frequency analysis graph that is prepared based on the norm distribution graph shown in FIG. 13 in accordance with the procedure described above. By detecting f2 values inside a circle shown in FIG. 17, it can be determined that the subject is suffering from aneurysm.

Figure 18:
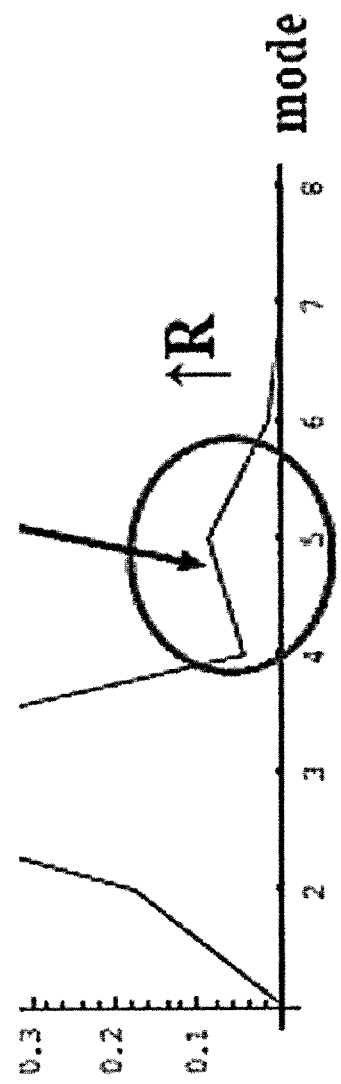
FIG. 18 is a diagram illustrating R (Norm value of Mode 5/Norm value of Mode 4).

Incidentally, FIG. 18 is one illustrated by extracting a part of FIG. 13, as for mode 5/mode 4 (f2) that is the vertical axis of FIG. 17. In this case, in order to evaluate a peak of mode 5, a ratio of mode 5 to mode 4 (Norm value of mode 5/Norm value of mode 4) is defined as R. When R is observed, R increases in the process of transition from a state in which there is no arteriosclerosis to a state in which arteriosclerosis is mild; and R decreases in the process of transition from a state in which arteriosclerosis is mild to a state in which arteriosclerosis is severe. Accordingly, based on the relationship between f1 and R, it is possible to diagnose not only the progress of arteriosclerosis, but also aneurysm and narrowing of blood vessels (infarction), which would be associated with the aneurysm. Furthermore, such a diagnosis can be achieved as reproducible automated analysis without involving human judgments in measurement and waveform analysis.

According to another aspect of the present invention, provided is a computer-readable storage medium in which the program of the present invention is stored. The type of the medium is not specifically restricted, even though magnetic or electrical media are available. The program of the present invention is recorded in accordance with the type of the medium. As for the record method, methods known in the art can be employed without limitation.

According to another aspect of the present invention, it is possible to provide a vascular disease determination device that uses the vascular disease determination program of the present invention to determine vascular disease in a subject. Such a device may employ a constitution as described below:
(1) means for obtaining a wavelet spectrum by performing a discrete wavelet transform on a waveform of a reflected echo that is obtained by transmitting ultrasonic waves to beating blood vessels of a subject;
(2) means for performing mode decomposition of the wavelet spectrum obtained by the means (1) to obtain a plurality of spectrums classified by mode;

(3) means for performing an inverse wavelet transform on the plurality of classified-by-mode spectrums obtained by the means (2) to obtain a plurality of corresponding waveforms classified by mode;
(4) means for calculating, from the plurality of classified-by-mode waveforms obtained by the means (3), a plurality of corresponding norm values;
(5) means for outputting a norm distribution graph by plotting the plurality of norm values calculated by the means (4) for each of corresponding modes;
(6) means for comparing the norm distribution graph output by the means (5) with a norm distribution graph obtained from a normal individual to detect that the norm distribution graphs match, or differ from, each other; and
(7) means for determining that the subject has vascular disease in the case where a difference between the norm distribution graphs is detected by the means (6).

According to another aspect of the present invention, it is possible to provide an arteriosclerosis progress evaluation device that uses the arteriosclerosis progress evaluation program of the present invention to evaluate progress of arteriosclerosis in a subject. Such a device may employ a constitution as described below:
(a) means for obtaining a wavelet spectrum by performing a discrete wavelet transform on a waveform of a reflected echo that is obtained by transmitting ultrasonic waves to beating blood vessels of a subject;
(b) means for performing mode decomposition of the wavelet spectrum obtained by the means (a) to obtain a plurality of spectrums classified by mode;
(c) means for performing an inverse wavelet transform on the plurality of classified-by-mode spectrums obtained by the means (b) to obtain a plurality of corresponding waveforms classified by mode;
(d) means for calculating, from the plurality of classified-by-mode waveforms obtained by the means (c), a plurality of corresponding norm values;
(e) means for outputting a norm distribution graph by plotting the plurality of norm values calculated by the means (d) for each of corresponding modes;
(f) means for detecting f1, which is a mode in which a peak value is observed on the norm distribution graph output by the means (e);
(g) means for constituting a two-dimensional attractor from a waveform of a reflected echo that is obtained by transmitting ultrasonic waves to beating blood vessels of a subject;
(h) means for calculating entropy from a probability of a trajectory represented by the two-dimensional attractor constituted by the means (g);
(i) means for outputting an entropy-average mode distribution graph that is obtained by plotting the entropy calculated by the means (h) to a mode around f1 detected by the means (f); and
(j) means for comparing the entropy-average mode distribution graph output by the means (i) with an entropy-average mode distribution graph obtained from a normal individual, and evaluating the progress of arteriosclerosis in the subject based on how much the entropy increases.

The vascular disease determination device and arteriosclerosis progress evaluation device of the present invention are devices that allow the above-mentioned programs of the present invention to be realized. The vascular disease determination device and arteriosclerosis progress evaluation device of the present invention may exist independently, or may be constituted as one device having the means and functions of the two. In the present specification, the vascular disease determination device and arteriosclerosis progress evaluation device of the present invention are collectively referred to as "device of the present invention." The device of the present invention may be constituted by equipping ultrasonic blood flow meter TRY-1 (TAIYO DENSHI Co., Ltd.) with the program of the present invention, for example.

By measuring at a plurality of points by using the device of the present invention, it is possible to detect symptoms that are difficult to measure in the case of one-point measurement. That is, the device of the present invention can employ a simultaneous multi-point measurement manner.

Figure 19:
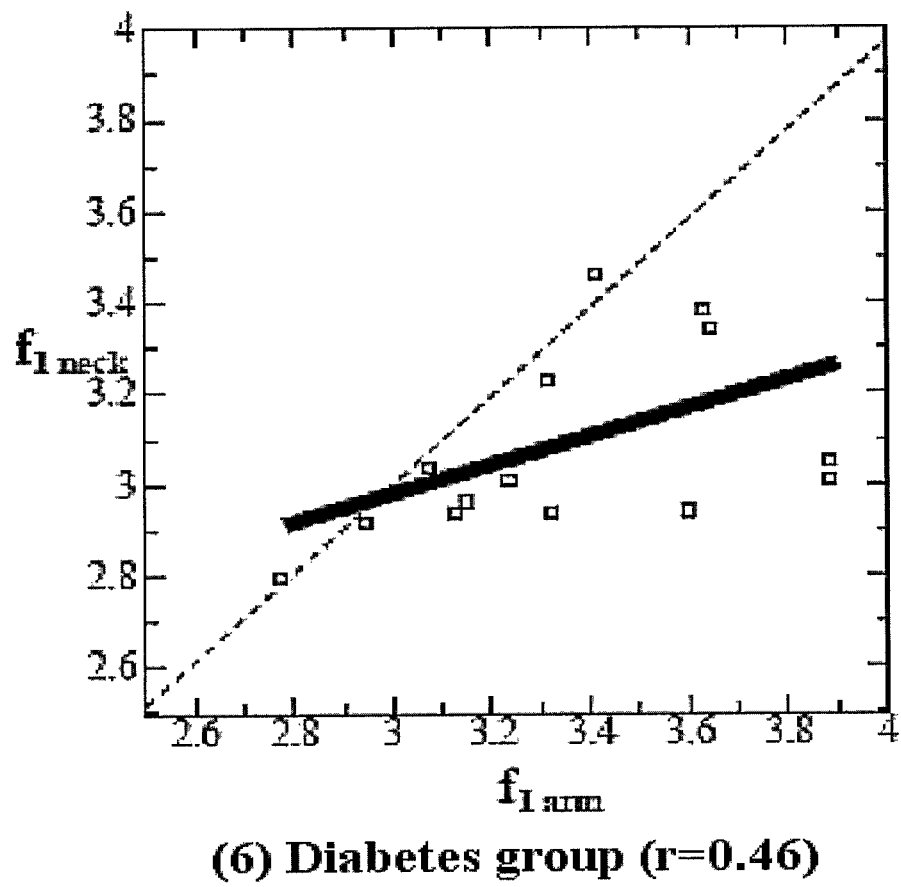
FIG. 19 is a diagram showing results of measuring the neck and wrist of a patient with diabetes by using the device of the present invention.

For example, it is possible for the device of the present invention to evaluate vascular disease in a subject by using, as measurement sites, the neck and wrist that are originally pointed out to be unable to clinically obtain an organ correlation of arteriosclerosis. In fact, FIG. 19 shows results of measuring the necks and wrists of people with diabetes who was assumed to be suffering from some kind of vascular disease, and of people who were not suffering from diabetes with the use of the device of the present invention. As shown in FIG. 19, as for f1, an organ correlation could not be obtained at an early stage for people who were not suffering from diabetes. However, in the cases of people with diabetes, a correlation of arteriosclerosis was obtained at the neck and the wrist, and it was demonstrated that there was more progress at the neck. The findings mean that arteriosclerosis starts to appear at the neck, and the progress thereof then quickly spreads to the entire body in the case of diabetes. The simultaneous multi-point measurement with the use of the device of the present invention makes it possible to obtain such symptoms for the first time. The measurement by the device of the present invention clinically has a significant meaning because the progress of arteriosclerosis can be diagnosed from various perspectives in relation with primary etiology. That is, the use of the device of the present invention makes it possible to identify primary locations of arteriosclerosis and aneurysm through local diagnosis of arteriosclerosis and diagnosis that is based on the organ correlation. Incidentally, PWV, which is disclosed in Non-Patent Document 1, offers comprehensive diagnosis, and therefore is not able to measure an organ correlation.

An operating method of a vascular disease determination device of the present invention for example includes the following steps:
(1) a step of obtaining a wavelet spectrum by performing a discrete wavelet transform on a waveform on a reflected echo that is obtained by transmitting ultrasonic waves to beating blood vessels of a subject;
(2) a step of performing mode decomposition of the wavelet spectrum obtained by the step (1) to obtain a plurality of spectrums classified by mode;
(3) a step of performing an inverse wavelet transform on the plurality of classified-by-mode spectrums obtained by the step (2) to obtain a plurality of corresponding waveforms classified by mode;
(4) a step of calculating, from the plurality of classified-by-mode waveforms obtained by the step (3), a plurality of corresponding norm values;
(5) a step of outputting a norm distribution graph by plotting the plurality of norm values calculated by the step (4) for each of corresponding modes;
(6) a step of comparing the norm distribution graph output by the step (5) with a norm distribution graph obtained from a normal individual to detect that the norm distribution graphs match, or differ from, each other; and
(7) a step of determining that the subject has vascular disease in the case where a difference between the norm distribution graphs is detected by the step (6).

An operating method of an arteriosclerosis progress evaluation device of the present invention for example includes the following steps:

(a) a step of obtaining a wavelet spectrum by performing a discrete wavelet transform on a waveform of a reflected echo that is obtained by transmitting ultrasonic waves to beating blood vessels of a subject;
(b) a step of performing mode decomposition of the wavelet spectrum obtained by the step (a) to obtain a plurality of spectrums classified by mode;
(c) a step of performing an inverse wavelet transform on the plurality of classified-by-mode spectrums obtained by the step (b) to obtain a plurality of corresponding waveforms classified by mode;
(d) a step of calculating, from the plurality of classified-by-mode waveforms obtained by the step (c), a plurality of corresponding norm values;
(e) a step of outputting a norm distribution graph by plotting the plurality of norm values calculated by the step (d) for each of corresponding modes;
(f) a step of detecting f1, which is a mode in which a peak value is observed on the norm distribution graph output by the step (e);
(g) a step of constituting a two-dimensional attractor from a waveform of a reflected echo that is obtained by transmitting ultrasonic waves to beating blood vessels of a subject;
(h) a step of calculating entropy from a probability of a trajectory represented by the two-dimensional attractor constituted by the step (g);
(i) a step of outputting an entropy-average mode distribution graph that is obtained by plotting the entropy calculated by the step (h) to a mode around f1 detected by the step (f); and
(j) a step of comparing the entropy-average mode distribution graph output by the step (i) with an entropy-average mode distribution graph obtained from a normal individual, and evaluating the progress of arteriosclerosis in the subject based on how much the entropy increases.

The operation methods of the device of the present invention can be easily performed by a computer after an appropriate computer program (or software) for processing data in the above-mentioned procedure is prepared. Such a computer program itself can be useful as a program that can be used to carry out the operating methods of the device of the present invention. One example of such a computer program is the program of the present invention.

According to the programs, media, and devices of the present invention, the "subject" and "normal individual" are not specifically restricted. However, for example, mammals, such as human beings, rats, mice, rabbits, dogs, and cats, are available. It is preferred that the "subject" and "normal individual" be human beings.

The programs, media, and devices of the present invention can be employed not only in clinical situations, but also in tests, research, and other situations. The programs, media, and devices of the present invention also can be used not only by doctors and other clinical experts, but also by assistants to experts, manufacturers of the devices, and other people without limitation. If the programs, media, and devices of the present invention are used in clinical situations, the programs, media, and devices can be used at any stage before diagnosis by doctors, in the middle of diagnosis by doctors, or after diagnosis by doctors. Accordingly, the programs, media, and devices of the present invention can be used as preliminary determination means with the aim of preventing vascular diseases such as arteriosclerosis, narrowing of blood vessels, and aneurysm. Furthermore, the programs, media, and devices of the present invention can be used as post-treatment determination means with the aim of preventing the recurrence of vascular disease after treatment. If the results of determination by the programs, media, and devices of the present invention, and the results of diagnosis by doctors are used in combination, it is possible to detect vascular diseases such as arteriosclerosis, narrowing of blood vessels, and aneurysm with a very high level of accuracy.

The invention claimed is:

1. A non-transitory computer readable medium storing a program for determining vascular disease in a subject, the program when executed causes a processor to perform the steps of:
   (1) obtaining a wavelet spectrum by performing a discrete wavelet transform on a waveform of a reflected echo that is obtained by transmitting ultrasonic waves to beating blood vessels of a subject;
   (2) performing mode decomposition of the wavelet spectrum obtained by the step (1) to obtain a plurality of spectrums classified by mode;
   (3) performing an inverse wavelet transform on the plurality of classified-by-mode spectrums obtained by the step (2) to obtain a plurality of corresponding waveforms classified by mode;
   (4) calculating, from the plurality of classified-by-mode waveforms obtained by the step (3), a plurality of corresponding norm values;
   (5) outputting a norm distribution graph by plotting the plurality of norm values calculated by the step (4) for each of corresponding modes;
   (6) comparing the norm distribution graph output by the step (5) with a norm distribution graph obtained from a normal individual to detect that the norm distribution graphs match, or differ from, each other; and
   (7) determining that the subject has vascular disease in the case where a difference between the norm distribution graphs is detected by the step (6).

2. The non-transitory computer readable medium storing the program according to claim 1, wherein the vascular disease is arteriosclerosis, narrowing of blood vessels, or aneurysm.

3. The non-transitory computer readable medium storing the program according to claim 1, wherein the vascular disease is arteriosclerosis, and the difference between the norm distribution graphs is a difference in f1, which is a mode in which a peak value on a norm distribution graph is observed.

4. The non-transitory computer readable medium storing the program according to claim 1, wherein the vascular disease is aneurysm, and the difference between the norm distribution graphs is a difference in the number of peaks on a norm distribution graph.

5. A non-transitory computer readable medium storing a program for evaluating progress of arteriosclerosis in a subject, the program when executed causes a processor to perform the steps of:
   (a) obtaining a wavelet spectrum by performing a discrete wavelet transform on a waveform of a reflected echo that is obtained by transmitting ultrasonic waves to beating blood vessels of a subject;
   (b) performing mode decomposition of the wavelet spectrum obtained by the step (a) to obtain a plurality of spectrums classified by mode;
   (c) performing an inverse wavelet transform on the plurality of classified-by-mode spectrums obtained by the step (b) to obtain a plurality of corresponding waveforms classified by mode;

(d) calculating, from the plurality of classified-by-mode waveforms obtained by the step (c), a plurality of corresponding norm values;

(e) outputting a norm distribution graph by plotting the plurality of norm values calculated by the step (d) for each of corresponding modes;

(f) detecting f1, which is a mode in which a peak value is observed on the norm distribution graph output by the step (e);

(g) constituting a two-dimensional attractor from a waveform of a reflected echo that is obtained by transmitting ultrasonic waves to beating blood vessels of a subject;

(h) calculating entropy from a probability of a trajectory represented by the two-dimensional attractor constituted by the step (g);

(i) outputting an entropy-average mode distribution graph that is obtained by plotting the entropy calculated by the step (h) to a mode around f1 detected by the step (f); and (j) comparing the entropy-average mode distribution graph output by the step (i) with an entropy-average mode distribution graph obtained from a normal individual, and evaluating the progress of arteriosclerosis in the subject based on how much the entropy increases.

6. A non-transitory computer-readable storage medium comprising the non-transitory computer readable medium storing the program according to any one of claims 1 to 5.

7. A vascular disease determination device for determining vascular disease in a subject, comprising:

(1) a processing device configured to obtain a wavelet spectrum by performing a discrete wavelet transform on a waveform of a reflected echo that is obtained by transmitting ultrasonic waves to beating blood vessels of a subject;

(2) a processing device configured to perform mode decomposition of the wavelet spectrum obtained by the processing device (1) to obtain a plurality of spectrums classified by mode;

(3) a processing device configured to perform an inverse wavelet transform on the plurality of classified-by-mode spectrums obtained by the processing device (2) to obtain a plurality of corresponding waveforms classified by mode;

(4) a processing device configured to calculate, from a plurality of classified-by-mode waveforms obtained by the processing device (3), a plurality of corresponding norm values;

(5) a processing device configured to output a norm distribution graph by plotting the plurality of norm values calculated by the processing device (4) for each of corresponding modes;

(6) a processing device configured to compare the norm distribution graph output by the processing device (5) with a norm distribution graph obtained from a normal individual to detect that the norm distribution graphs match, or differ from, each other; and (7) a processing device configured to determine that the subject has vascular disease in the case where a difference between the noun distribution graphs is detected by the processing device (6).

8. The device according to claim 7, wherein the vascular disease is arteriosclerosis, narrowing of blood vessels, or aneurysm.

9. The device according to claim 7, wherein the vascular disease is arteriosclerosis, and the difference between the norm distribution graphs is a difference in f1, which is a mode in which a peak value on a norm distribution graph is observed.

10. The device according to claim 7, wherein the vascular disease is aneurysm, and the difference between the norm distribution graphs is a difference in the number of peaks on a norm distribution graph.

11. An arteriosclerosis progress evaluation device for evaluating progress of arteriosclerosis in a subject, comprising:

(a) a processing device configured to obtain a wavelet spectrum by performing a discrete wavelet transform on a waveform of a reflected echo that is obtained by transmitting ultrasonic waves to beating blood vessels of a subject;

(b) a processing device configured to perform mode decomposition of the wavelet spectrum obtained by the processing device (a) to obtain a plurality of spectrums classified by mode;

(c) a processing device configured to perform an inverse wavelet transform on the plurality of classified-by-mode spectrums obtained by the processing device (b) to obtain a plurality of corresponding waveforms classified by mode;

(d) a processing device configured to calculate, from the plurality of classified-by-mode waveforms obtained by the processing device (c), a plurality of corresponding norm values;

(e) a processing device configured to output a norm distribution graph by plotting the plurality of norm values calculated by the processing device (d) for each of corresponding modes;

(f) a processing device configured to detect f1, which is a mode in which a peak value is observed on the noun distribution graph output by the processing device (e);

(g) a processing device configured to constitute a two-dimensional attractor from a waveform of a reflected echo that is obtained by transmitting ultrasonic waves to beating blood vessels of a subject;

(h) a processing device configured to calculate entropy from a probability of a trajectory represented by the two-dimensional attractor constituted by the processing device (g);

(i) a processing device configured to output an entropy-average mode distribution graph that is obtained by plotting the entropy calculated by the processing device (h) to a mode around f1 detected by the processing device (f); and (j) a processing device configured to compare the entropy-average mode distribution graph output by the processing device (i) with an entropy-average mode distribution graph obtained from a normal individual, and evaluating the progress of arteriosclerosis in the subject based on how much the entropy increases.

* * * * *